(12) United States Patent
Huhtala et al.

(10) Patent No.: US 6,388,090 B2
(45) Date of Patent: May 14, 2002

(54) IMIDAZOLE DERIVATIVES

(75) Inventors: Paavo Huhtala; Arto Karjalainen, both of Espoo; Antti Haapalinna, Turku; Jyrki Lehtimäki, Sauvo; Arja Karjalainen, Espoo; Raimo Virtanen, Rusko, all of (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 09/758,350

(22) Filed: Jan. 12, 2001

Related U.S. Application Data

(60) Provisional application No. 60/176,029, filed on Jan. 14, 2000.

(51) Int. Cl.$^7$ ............... C07D 233/54; A61K 31/4164
(52) U.S. Cl. ............... 548/311.1; 548/312.1; 514/396; 514/397; 514/399
(58) Field of Search ............ 548/311.1, 312.1; 514/396, 397, 399

(56) References Cited

U.S. PATENT DOCUMENTS

| | | | | |
|---|---|---|---|---|
| 4,689,339 A | * | 8/1987 | Karjalainen et al. | 514/396 |
| 4,910,214 A | * | 3/1990 | Karjalainen et al. | 514/396 |
| 4,933,359 A | * | 6/1990 | Karjalainen et al. | 514/396 |
| 5,434,177 A | | 7/1995 | Riekkinen et al. | 514/399 |
| 5,498,623 A | | 3/1996 | Karjalainen et al. | 514/396 |
| 5,541,211 A | | 7/1996 | Pertovaara et al. | 514/396 |
| 5,658,938 A | | 8/1997 | Geerts et al. | 514/400 |

FOREIGN PATENT DOCUMENTS

| | | |
|---|---|---|
| EP | 0 183 492 | 6/1986 |
| GB | 2 225 782 | 6/1990 |
| WO | WO 97/12874 | 4/1997 |
| WO | WO 99/28300 | 6/1999 |
| WO | WO 00/07997 | 2/2000 |
| WO | WO 01/00586 | 1/2001 |

OTHER PUBLICATIONS

Sommer et al., "Application of (2–Cyanoaryl)arylacetonitriles in Cyclization and Annulation Reactions. Preparation of 3–Arylindans, 4–Aryl–3,4–dihydronaphthalenes, 4–Aryl-isoquinolines, 1–Aminonaphthalenes, and Heterocyclic Analogues," J. Org. Chem., vol. 55, pp. 4822–4827 (1990).

Welch et al., "Nontricyclic Antidepressant Agents Derived from cis– and trans–1–Amino–4–aryltetralins," J. Med. Chem., vol. 27, pp. 1508–1515 (1984).

Klaus P. Bøgesø, "Neuroleptic Activity and Dopamine–Uptake Inhibition in 1–Piperazino–3–phenylindans," J. Med. Chem., vol. 26, pp. 935–947 (1983).

Miller et al., "the Thermolysis of Substituted Indenes. Sigmatropic Phenyl and Hydrogen Migrations," J. Chem. Soc., vol. 93, pp. 650–656 (1971).

Smonou et al., "Convenient Synthetic Sequence for the Preparation of Indanones," Synthetic Communications, vol. 20(9), pp. 1387–1397 (1990).

Kenneth L. Kirk, "4–Lithio–1–tritylimidazole as a Synthetic Intermediate. Synthesis of Imidazole–4–carboxaldehyde," J. Heterocyclic Chem., vol. 22, pp. 57–59 (1985).

* cited by examiner

Primary Examiner—T. A. Solola
Assistant Examiner—Golam M. M. Shameem
(74) Attorney, Agent, or Firm—Finnegan, Henderson, Farabow, Garrett, Dunner, L.L.P.

(57) ABSTRACT

An imidazole derivative of formula (I)

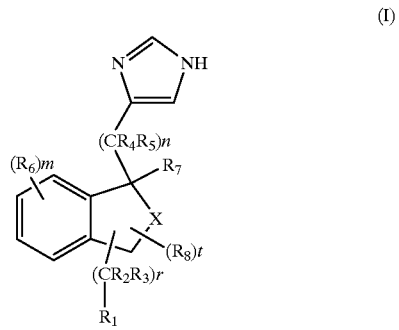

or a pharmaceutically acceptable salt or derivative thereof. The compounds of formula I exhibit affinity for alpha2 adrenoceptors.

23 Claims, No Drawings

IMIDAZOLE DERIVATIVES

This application claims the benefit of priority under 35 U.S.C. § 119(e) to U.S. Provisional Application No. 60/176, 029, filed on Jan. 14, 2000, the entire contents of which are incorporated by reference herein.

BACKGROUND OF THE INVENTION

The present invention relates to new pharmacologically active imidazole derivatives and pharmaceutically acceptable salts and esters thereof, as well as to processes for their preparation and to pharmaceutical compositions containing them.

It is known that several derivatives of imidazole have affinity for alpha1 and/or alpha2 adrenoceptors. Accordingly, WO-A-97 12874 describes imidazole-substituted (1,2,3,4-tetrahydro-1-naphthalenyl)- and (2,3-dihydro-1H-inden-1-yl)-derivatives which are stated to possess affinity for alpha2 adrenoceptors, most of them being selective alpha2 adrenoceptor agonists. EP-A-0 717 037 describes 4-(1,2,3,4-tetrahydro-1-naphthalenyl)- and 4-(2,3-dihydro-1H-inden-1-yl)-1H-imidazole derivatives which possess alfa2 adrenoceptor agonistic and alpha1 adrenoceptor antagonistic activity. On the other hand, the imidazole derivatives disclosed in EP-A-0 183 492 are known as selective alpha2 adrenoceptor antagonists. Compounds acting on the said alpha adrenoceptors may exert a wide variety of peripheral and/or CNS (central nervous system) effects in mammals.

SUMMARY OF THE INVENTION

The inventors have now found that the present imidazole derivatives of the invention exhibit affinity for alpha2 adrenoceptors so that they can be useful in the treatment of various disorders or diseases wherein the alpha2 adrenoceptors are involved. Such disorders or diseases include various disorders of the central nervous system (CNS), i.e. neurological, psychiatric or cognition disorders, as well as various disorders of the pheripheric system, e.g. diabetes, orthostatic hypotension, lipolytic disorders (such as obesity) or sexual dysfunction.

DETAILED DESCRIPTION OF THE INVENTION

The imidazole derivatives of the invention can be represented by the following formula (I):

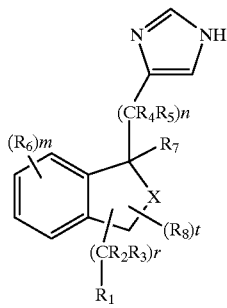

(I)

wherein
X is —$CH_2$—$(CH_2)_p$—, —O—, =NH or —S—;
$R_1$ is phenyl, naphthyl, 1,2,3,4-tetrahydronaphthyl, $C_3$-$C_7$-cycloalkyl, $C_5$-$C_7$-cycloalkenyl, $C_5$-$C_7$-cycloalkynyl or mono- or bicyclic aromatic or partially or fully saturated heterocyclic group with 5 to 10 ring atoms which consist of carbon atoms and one to three heteroatoms selected from N, O and S;

wherein the said phenyl, naphthyl,1,2,3,4-tetrahydronaphthyl, $C_3$-$C_7$-cycloalkyl, $C_5$-$C_7$-cycloalkenyl, $C_5$-$C_7$-cycloalkynyl or mono- or bicyclic aromatic or partially or fully saturated heterocyclic group is optionally substituted with one to three substituents selected independently from halogen, —OH, —$NH_2$, halo-$C_1$-$C_6$-alkyl, $C_1$-$C_6$-alkyl, $C_2$-$C_6$-alkenyl, $C_2$-$C_6$-alkynyl, $C_1$-$C_6$-alkoxy, OH—($C_1$-$C_6$)-alkyl, $NH_2$—($C_1$-$C_6$)-alkyl and mono- or di($C_1$-$C_6$-alkyl) amino;

$R_2$ is H or $C_1$-$C_6$-alkyl;

$R_3$ is H or $C_1$-$C_6$-alkyl; and $R_4$ is H or $C_1$-$C_6$-alkyl;

$R_5$ is H, or $R_5$ and $R_7$ form together a bond;

each $R_6$ is independently halogen, —OH, —$NH_2$, halo-$C_1$-$C_6$-alkyl, $C_1$-$C_6$-alkyl, $C_1$-$C_6$-alkoxy or OH—($C_1$-$C_6$)-alkyl;

$R_7$ is H, OH or $C_1$-$C_4$-alkyl, or $R_7$ and $R_5$ form together a bond;

each $R_8$ is independently OH, $C_1$-$C_6$-alkyl, halo-$C_1$-$C_6$-alkyl or $C_1$-$C_6$-alkoxy;

m is 0,1,2 or 3;

n is 0 or 1;

p is 0 or 1;

r is 0 or 1;

t is 0,1 or 2;

or pharmaceutically acceptable esters or salts thereof.
When X is —$CH_2$—$(CH_2)_p$— and p is 0, or when X is =NH,

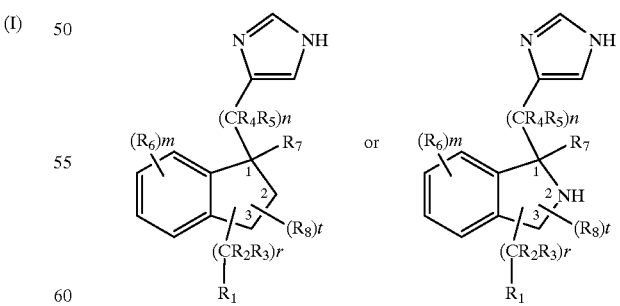

then the bulky substituent —($CR_2R_3$)r— $R_1$ is preferably at the 2- or 3-position of the 5-ring moiety (whereby, of course, in the above formulae the H-atom attached to ring carbon atom or, respectively, ring nitrogen atom will be replaced by the said substituent).

When X is —CH$_2$—(CH$_2$)$_p$— and p is 1,

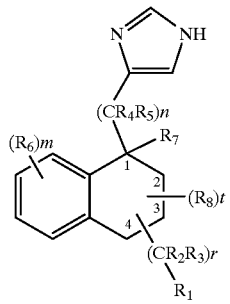

then the bulky substituent —(CR$_2$R$_3$)r—R$_1$ is preferably at the 3- or 4-position of the 6-ring moiety.

The following subgroups (1) to (17) of compounds of formula I taken alone or in any combination with each other are preferred:

1) n is 0;
2) n is 1;
3) n is 1 and R$_4$ and R$_5$ are H;
4) r is 0;
5) r is 1 and R$_2$ and R$_3$ are independently H or C$_1$-C$_4$-alkyl; preferably H;
6) t is 0;
7) R$_7$ is H;
8) X is —CH$_2$—(CH$_2$)$_p$—; and p is 0 or 1;
9) X is —CH$_2$—(CH$_2$)$_p$— and p is 0;
10) X is —CH$_2$—(CH$_2$)$_p$— and p is 1;
11) X is —O—;
12) R$_1$ is phenyl, naphthyl, 1,2,3,4-tetrahydronaphthyl, C$_5$-C$_7$-cycloalkyl, C$_5$-C$_7$-cycloalkenyl, C$_5$-C$_7$-cycloalkynyl, pyridyl, pyrimidinyl, thienyl, furyl, cyclohexyl, piperidyl, piperazinyl or morpholinyl; preferably R$_1$ is phenyl, naphthyl, pyridyl, thienyl, furyl or cyclohexyl; e.g. R$_1$ is phenyl; or e.g. R$_1$ is cyclohexyl;
13) R$_1$ is as defined above in subgroup (12) substituted with one to three of the substituents selected independently from halogen, —OH, —NH$_2$, halo-C$_1$-C$_6$-alkyl, C$_1$-C$_6$-alkyl, C$_2$-C$_6$-alkenyl, C$_2$-C$_6$-alkynyl and C$_1$-C$_6$-alkoxy; preferably with one to three, e.g. one or two, of the substituents selected independently from halogen, —OH, C$_1$-C$_6$-alkoxy and C$_1$-C$_6$-alkyl; more preferably from F, —OH and C$_1$-C$_6$-alkoxy;
14) m is 0; or m is 1 or 2;
15) m is 1 or 2 and each R$_6$ is independently halogen, —OH, C$_1$-C$_6$-alkoxy or C$_1$-C$_6$-alkyl; preferably F, —OH or C$_1$-C$_6$-alkoxy;
16) n is 0 and X is —CH$_2$—(CH$_2$)$_p$—; and/or
17) n is 1 and X is —CH$_2$—(CH$_2$)$_p$—, —O—, =NH or —S—, e.g. —CH$_2$—(CH$_2$)$_p$— or —O—.

Preferred subgroups of compounds of formula I are, for example,

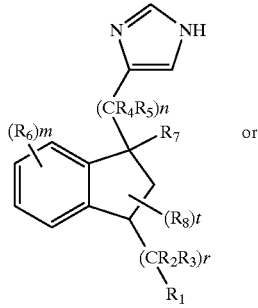

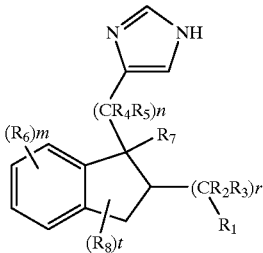

wherein R$_1$ to R$_8$, m, n, r and t are as defined above.

In a subgroup of the compounds of formula I, IA or IB, r is 0, or r is 1 and R$_2$ and R$_3$ are H. In a further subgroup of the compounds of formula I, IA or IB, n is 0, or n is 1 and R$_4$, R$_5$ and R$_7$ are H. Preferably, t is 0. The optional substituent R$_6$ is e.g. at 5- and/or 6-position of the indane ring system.

In a further preferred subgroup of the compounds I, IA or IB, R$_1$ is phenyl, naphthyl, pyridyl, thienyl, furyl or cyclohexyl, e.g. phenyl, pyridyl or cyclohexyl, such as phenyl or cyclohexyl, e.g. phenyl, each of which is optionally substituted with one to three, e.g. one or two, of the substituents selected independently from halogen, —OH, —NH$_2$, halo-C$_1$-C$_6$-alkyl, C$_1$-C$_6$-alkyl, C$_2$-C$_6$-alkenyl, C$_2$-C$_6$-alkynyl, C$_1$-C$_6$-alkoxy, OH—(C$_1$-C$_6$)-alkyl, NH$_2$—(C$_1$-C$_6$)-alkyl and mono- or di(C$_1$-C$_6$-alkyl)amin; e.g. from halogen, —OH, C$_1$-C$_6$-alkoxy and C$_1$-C$_6$-alkyl; preferably from F, —OH and C$_1$-C$_6$-alkoxy.

In a further preferred subgroup of the compounds I, IA or IB m is 0, or m is 1 or 2 and each R$_6$ is independently halogen, —OH or C$_1$-C$_6$-alkoxy.

A further subgroup of the compounds of formula I are compounds of formula IC or ID

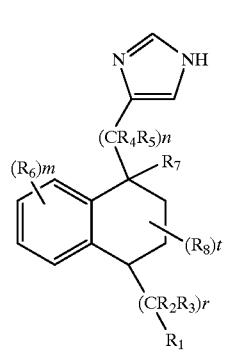

-continued (ID)

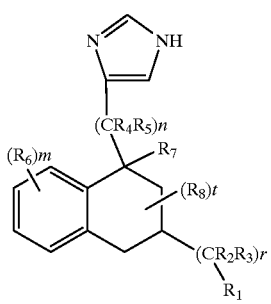

wherein $R_1$ to $R_8$, m, n, r and t are as defined above.

A further subgroup of the compounds of formula I are compounds of formula IE (IE)

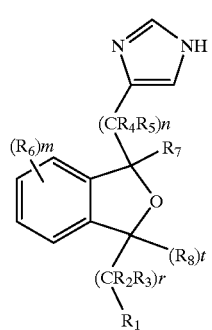

wherein $R_1$ to $R_8$, m, n and r are as defined above and t is 0 or 1.

Terms as employed herein have the following meanings: A halogen or halo is e.g. fluorine, chlorine, bromine or iodine, preferably fluorine or chlorine, more preferably fluorine. The term $C_1$-$C_6$-alkyl group as employed herein as such or as part of another group includes both straight and branched chain radicals of up to 6 carbon atoms, and preferably of 1 to 4 carbon atoms. The term $C_1$-$C_6$-alkoxy refers to —O($C_1$-$C_6$-alkyl) wherein $C_1$-$C_6$-alkyl is as defined above. The term $C_2$-$C_6$-alkenyl includes both straight and branched chain radicals of up to 6 carbon atoms, preferably of 2 to 4 carbon atoms, containing double bond (s). The term $C_2$-$C_6$-alkynyl includes both straight and branched chain radicals of up to 6 carbon atoms, preferably of 2 to 4 carbon atoms, containing triple bond(s). The term halo- $C_1$-$C_6$-alkyl refers to $C_1$-$C_6$-alkyl radical, as defined above, that is substituted by one or more halo radicals as defined above, e.g. trifluoromethyl, difluoromethyl etc. The term $C_3$-$C_7$-cycloalkyl means cyclopropyl, cyclobutyl, cyclopentyl, cyclohexyl or cycloheptyl. $C_5$-$C_7$-cycloalkyl means cyclopentyl, cyclohexyl or cycloheptyl, preferably cyclopentyl or cyclohexyl. $C_5$-$C_7$-cycloalkenyl or $C_5$-$C_7$-cycloalkynyl refers to $C_5$-$C_7$-cycloalkyl as defined above, containing double bond(s) or, respectively, a triple bond in its ring structure. Mono- or bicyclic aromatic or partially or fully saturated heterocyclic group from 5 to 10 ring atoms, preferably from 5 to 6 ring atoms, which consists of carbon atoms and one to three, preferably one to two, heteroatoms selected from N, O and/or S, refers e.g. to pyridyl, pyrimidinyl, thienyl, furyl, piperidinyl, piperazinyl or morpholinyl, preferably to pyridyl, thienyl or furyl.

The compounds of formula I and the subgroups IA, IB, IC, ID and IE thereof, as well as the pharmaceutically acceptable esters and salts thereof, are referred to below as the compounds of the invention, unless otherwise indicated.

The compounds of the invention may have chiral carbon atom(s) in their structure. The invention includes within its scope all the possible stereoisomers of the compounds I, including geometric isomers, e.g. Z and E isomers (cis and trans isomers), and optical isomers, e.g. diastereomers and enantiomers. Furthermore, the invention includes in its scope both the individual isomers and any mixtures thereof, e.g. racemic mixtures. The individual isomers may be obtained using the corresponding isomeric forms of the starting material or they may be separated after the preparation of the end compound according to conventional separation methods. For the separation of, for example, optical isomers, e.g. enantiomers, from the mixture thereof the conventional resolution methods, e.g. fractional crystallisation, may be used.

The compounds of the invention can form acid addition salts with both organic and inorganic acids well known in the field of pharmaceuticals. Typical acid addition salts are e.g. chlorides, bromides, sulfates, nitrates, phosphates, sulfonates, formates, tartrates, maleates, citrates, benzoates, salicylates, ascorbates. Furthermore, in the compounds of the invention, wherein $R_6$, $R_8$ and/or the optional substituent at the ring moiety as $R_1$ is OH, the said —OH functionality may form esters with pharmaceutically acceptable acids which are conventional in the field of pharmaceuticals and which retain the pharmacological properties of the free form. Examples of such esters include esters of aliphatic or aromatic alcohols, e.g. lower alkyl esters, e.g. methyl, ethyl and propyl esters.

The compounds of the invention can be prepared using e.g. the following methods. Accordingly:

(a) The preparation of, for example, compounds of formula 1, wherein n is 1, may be illustrated e.g. with the following reaction scheme A:

Scheme A

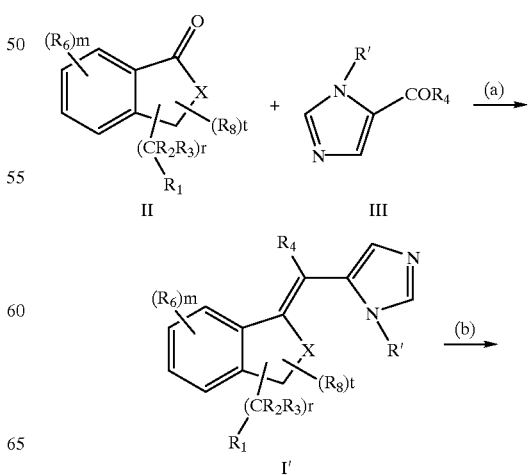

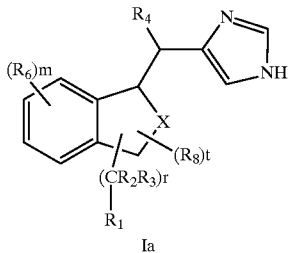

wherein X, $R_1$ to $R_4$, $R_6$, $R_8$, m, r and t are as defined above and R' is H or a conventional protecting group for =NH in the imidazole ring, e.g. benzyl, trityl (—CPh3) or $SO_2NMe_2$.

The step (a) is a conventional McMurry coupling reaction, i.e. a reductive carbonyl coupling of an imidazole carbaldehyde or an imidazolyl alkylketone III with a ketone II in the presence of a catalyst, e.g. titanium(0) (e.g. produced in situ), in an inert solvent, e.g. THF, at room or elevated temperature. The resulted compound of formula I, wherein $R_5$ and $R_7$ form together a bond (I'), may be deprotected, if necessary, and isolated according to the known methods, or converted by hydrogenation of the double bond to another compound of formula I, wherein $R_5$ and $R_7$ are H (Ia, step b). In the hydrogenation step (b) the possible protecting group in the imidazole ring is eliminated simultaneously. The compound of formula I obtained is isolated and worked up in a manner known in the art;

(b) The preparation of, for example, compounds of formula I, wherein n is 0 and $R_7$ is H, may be illustrated e.g. with the reaction scheme B:

Scheme B

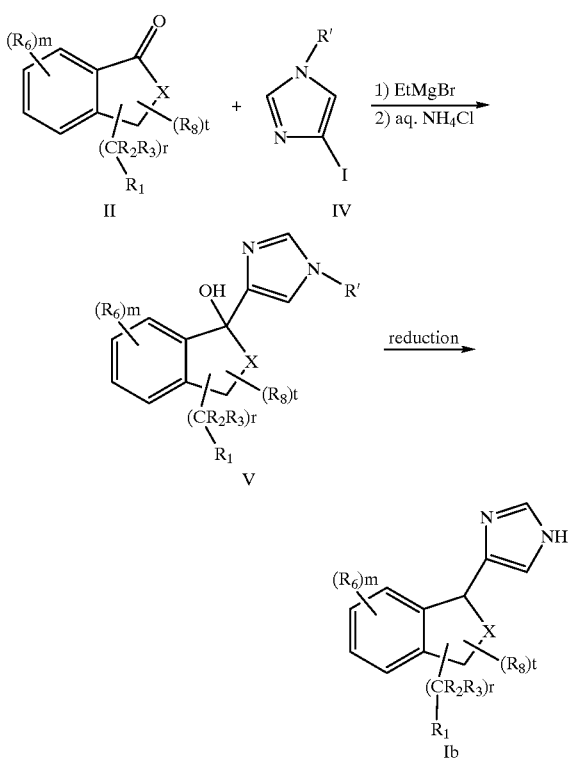

wherein X, $R_1$ to $R_3$, $R_6$ and $R_8$ m, r and t are as defined above and R' is a conventional protecting group for =NH in the imidazole ring, e.g. benzyl, trityl (—CPh3) or $SO_2NMe_2$.

In the reaction scheme B, a compound of formula II is first reacted with a compound of formula IV, in the presence of a Grignard-reagent, such as EtMgBr, in a suitable solvent, e.g. $CH_2Cl_2$, at dry reaction conditions, at room temperature or elevated temperature, and the reaction mixture obtained is then treated with an aqueous $NH_4Cl$-solution to obtain the compound of formula V. The hydroxyl group and the amino protecting group R' of the compound of formula V can be eliminated in a manner known in the art, e.g. using e.g. TMSCI—NaI—$CH_3CN$, in a suitable solvent, e.g. $CH_2Cl_2$, at room or elevated temperature. In the elimination step an intermediate indene-imidazole may be formed, which is further reduced in a manner known in the art. The compound of formula I (Ib) thus obtained is isolated using conventional methods.

(c) The preparation of, for example, compounds of formula I, wherein n is 0, may further be illustrated e.g. with the following reaction scheme C:

Scheme C

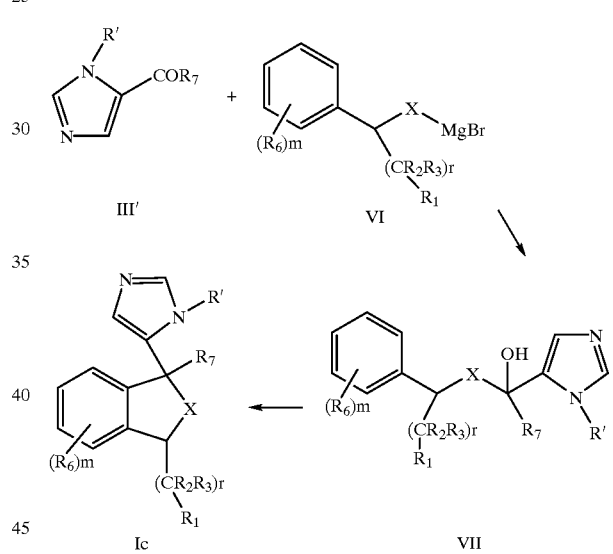

wherein $R_1$ to $R_3$, $R_6$, $R_7$, m and r are as defined above X is —$CH_2$—$(CH_2)_p$—, p is 0 or 1 and R' is a conventional protecting group for =NH in the imidazole ring, e.g. benzyl or trityl (—CPh3).

In the method of scheme C the compound III' is reacted with Grignard reagent VI at room or elevated temperature in a suitable solvent. The resulted compound VII is cyclized in a manner known in the art to obtain the end product Ic.

The other compounds of formula I not illustrated in the above schemes can be prepared according to or analogously to the methods described above or known in the prior art, starting from the suitable starting material. As to the prior art methods reference is made e.g. to WO-A-97 12874, the contents of which are hereby incorporated by reference.

The starting compounds II are commercially available or they may be prepared via a variety of known synthetic routes using suitable starting materials and conventional methods known to those skilled in the art. For instance the compounds of formula II, wherein X is —$CH_2$—$(CH_2)_p$—, p is 0 or 1, can be prepared according to or analogously to the methods described by Sommer, M. B. et al., J.Org.Chem., vol.55,1990, p.4822, Welch, W. M. et al., J.Med.Chem., vol.27,1984, p.1508, and/or Bøgesø, K. P., J.Med.Chem., vol.26, 1983, p.935, the contents of which are hereby incorporated by reference. As a further example, the preparation of compounds II can be carried out according to or analogously to the methods described in the abovementioned WO-A-97 12874, Miller L. L. and Boyer R. F., J.Am.Chem.Soc., vol.93(3), 1971, p.650–656, or Smonou I. and Orfanopoulos M., Synthetic Communications, vol.20 (9), 1990, p.1387–1397, which are also incorporated by reference herein.

As to the starting material III, III' and IV, these are commercially available, for example, in an unprotected form, or they may be prepared according to the methods known to those skilled in the art (cf., for example, Kirk, K. L, J.Heterocycl.Chem., vol.22,1985, 57). If necessary, the =NH of the imidazole can be protected using conventional methods and protecting groups (R'), e.g. benzyl or trityl. It is understood that, due to the tautomerism, the protecting group R' may be attached to either of the two nitrogen atoms of the imidazole ring.

If necessary, also $R_6$, $R_8$ and/or the optional substituent at the ring moiety as $R_1$ can be protected in a manner known in the art. Such protecting groups as well as the optional protecting group R' can be removed at the final stage using suitable conventional deprotection method(s) known in the art.

It should be noted that the above disclosed synthetic routes are meant to illustrate the preparation of the compounds of the invention and the preparation is by no means limited thereto, i.e. other synthetic processes which are within the general knowledge of a skilled person are also possible.

The compounds of the invention may be converted, if desired, into their pharmaceutically acceptable salt or ester form using methods well known in the art.

As already mentioned hereinbefore, the compounds of the invention show interesting pharmacological properties, namely they exhibit affinity for alpha2 adrenoceptors. The said activity of the compounds of the invention is demonstrated with the pharmacological test presented below.

Antagonist activity on alpha2 Adrenoceptors (Alpha2AR) in rat vas deferens in vitro Rats were killed by $CO_2$-suffocation. Vas deferentia were dissected out and both prostatic halves were removed to tissue chambers containing Krebs-solution of the following composition (mM): NaCl 118, KCl 4.7, $CaCl_2$ 2.5, $KH_2PO_4$ 1.2, $MgSO_4$ 0.6, $NaHCO_3$ 25, glucose 11.1, aerated by 5% carbogen, temperature 37° C., pH 7.4. Propranolol 260 g/l and desipramine 2 g/ml were added to prevent the possible effects on alpha-adrenergic receptors and to prevent re-uptake of released norepinephrine, respectively. Preparations were tied to the bottom hooks of the incubation chambers and then to isometric force-displacement transducers above. Electrical stimulation was started after the equilibrium period (5 minutes under a resting tension of 0.5 g) by introducing field stimulation with the following parameters: twin-pulses, voltage 70 V, frequency 0.2 Hz, delay 5 ms, duration 2 ms. As soon as the electrically induced twitch response was stabilised, the test compounds were administered by a cumulative fashion with half logarithmic increments at five minute intervals. Inhibition of the electrically evoked contractions was measured as the response to alpha2AR agonists. Antagonist was administered into the incubation medium at least five minutes before agonist. Means ± SEM of percentage inhibition were calculated in the absence and in the presence of antagonist and expressed as dose-response curves. In order to express the antagonist potency, the pA2-value was calculated. The results of the test are reported in Table 1.

TABLE 1

| Compound | vas deferens |
|---|---|
| | Alpha2 antagonistic activity |
| Compound 1 | pA2 = 7.0 |
| Compound 2 | pA2 = 6.0 |
| Compound 3 | pA2 = 5.6 |
| Compound 4 | pA2 = 6.9 |
| Compound 5 | pA2 = 6.3 |
| Compound 6 | pA2 = 6.6 |
| Compound 7 | pA2 = 7.6 |
| Compound 8 | pA2 = 6.7 |
| Compound 9 | pA2 = 6.2 |
| Compound 10 | pA2 = 6.2 |
| Compound 11 | pA2 = 6.2 |
| Compound 12 | pA2 = 6.3 |
| Compound 13 | pA2 = 5.6 |
| Compound 14 | pA2 = 5.5 |
| Compound 15 | pA2 = 6.2 |
| Compound 16 | pA2 = 6.5 |

In general, the compounds of the invention exhibiting alpha2-antagonistic activity may be useful for therapeutical indications in which alpha2-antagonists are used. They may also be used for reversal of the effects of alpha2-agonists.

Accordingly, the compounds of the invention may be useful, for example, in the treatment of different neurological, psychiatric and cognition disorders. Furthermore, they may be used in the treatment of various peripheral disorders, e.g. diabetes, orthostatic hypotension, lipolytic disorders (such as obesity) or sexual dysfunction.

The compounds of the invention may be administered enterally, topically or parenterally.

The compounds of the invention may be formulated alone or together with another active ingredient and/or together with a pharmaceutically acceptable diluent, carrier and/or excipient in different pharmaceutical unit dosage forms, e.g. tablets, capsules, solutions, emulsions and powders etc., depending on the route of administration, using conventional techniques. The pharmaceutically acceptable diluent, carrier and/or excipient can be selected from those conventionally used in the field of pharmaceuticals noticing the chosen route of administration.

The amount of the active ingredient varies from 0.01 to 75 weight-% depending on, for example, the type of the dosage form.

The specific dose level of the compounds of the invention depends on several factors such as the compound to be administered, the species, age and the sex of the subject to be treated, the condition to be treated and on the route and method of administration. Accordingly, the dosage for parenteral administration is typically from 0.5 µg/kg to 10 mg/kg per day and that for oral administration is from 5 µg/kg to 100 mg/kg for an adult male.

The present invention also provides a compound of the invention or an ester or salt thereof for use in a method of treatment of human or animal body.

The present invention further provides a compound of the invention or an ester or salt thereof for use in the treatment of different CNS-disorders, such as neurological, psychiatric and cognition disorders, or in the treatment of various peripheral disorders, e.g. diabetes, orthostatic hypotension, lipolytic disorders (such as obesity) or sexual dysfunction.

The invention also provides the use of a compound of the invention or an ester or salt thereof in the manufacture of a medicament for the treatment of different CNS-disorders, e.g. neurological, psychiatric and cognition disorders, or in the treatment of various peripheral disorders, e.g. diabetes, orthostatic hypotension, lipolytic disorders (such as obesity) or sexual dysfunction.

The invention further relates to a method for the treatment of different CNS-disorders, e.g. neurological, psychiatric and cognition disorders, or peripheral disorders, e.g. diabetes, orthostatic hypotension, lipolytic disorders (such as obesity) or sexual dysfunction, by administering to a subject in need of such treatment an effective amount of the compound of the invention or a pharmaceutically acceptable ester or salt thereof.

The present invention will be explained in more detail by the following examples. The examples are meant only for illustrating purposes and do not limit the scope of the invention which is defined in claims.

EXAMPLE 1

4-(6-Methoxy-3-phenylindan-1-ylmethyl)-1H-imidazole

Titanium(IV)chloride (7.4 ml) was added dropwise to a stirred suspension of zinc powder (8.8 g) in dry tetrahydrofuran (200 ml) with ice cooling under a nitrogen atmosphere. The resulting mixture was heated at reflux for 2 hr with stirring. A solution of 6-methoxy-3-phenyl-1-indanone (4.0 g) and 3-benzyl-3H-imidazole-4-carbaldehyde (4.5 g) in dry tetrahydrofuran (40 ml) was added, and the reflux was continued for 5 hr. The cooled reaction mixture was made alkaline with dilute sodium hydroxide solution. The slurry was filtered, and the filtrate was evaporated to dryness under reduced pressure. The residue was dissolved in acidic water and extracted with dichloromethane. The combined organic phase was washed with water and evaporated to dryness.

The crude intermediate (1-Benzyl-5-(6-methoxy-3-phenylindan-1-ylidenemethyl-1H-imidazole) was dissolved in a solution of ethanol (200 ml), water (20 ml) and hydrochloric acid (1.0 ml). The mixture was hydrogenated at 50–60° C. with 10% palladium on carbon as catalyst until no more hydrogen was consumed. The mixture was filtered, and the filtrate was evaporated to dryness. The residue was dissolved in water, made alkaline with sodium hydroxide solution and extracted with ethyl acetate. The combined organic phase was washed with water, dried with sodium sulfate and evaporated under reduced pressure to give a crude product of racemic cis and trans diastereoisomers. The product was purified by flash chromatography (elution with a dichloromethane—methanol gradient). The base product was dissolved in ethyl acetate and converted to its hydrochloride salt with hydrogen chloride gas dissolved in ethyl acetate.

$^1$H NMR (cis isomer as HCl-salt, DMSO-$d_6$): 1.62–1.70 (m, 1H), 2.50–2.57 (m, 1H), 2.82 (dd, J=14.7 Hz, J=9.5 Hz, 1H), 3.45 (dd, J=14.7 Hz, J=4.6 Hz, 1H), 3.48–3.56 (m, 1H), 3.75 (s, 3H), 4.16–4.21 (m, 1H), 6.67–7.34 (m, 8H), 7.46 (s, 1H), 9.03 (s, 1H)

$^1$H NMR (trans isomer as HCl-salt, DMSO-$d_6$): 2.08–2.17 (m,1H), 2.23–2.31 (m, 1H), 2.84 (dd, J=14.7 Hz, J=9.5 Hz, 1H), 3.12 (dd, J=14.7 Hz, J=4.6 Hz, 1H), 3.60–3.69 (m, 1H), 3.72 (s, 3H), 4.32–4.39 (m, 1H), 6.75–7.35 (m, 8H), 7.43 (s, 1H), 8.99 (s,1H)

Using the same method the following compounds were prepared:

4-(3-Phenylindan-1-ylmethyl)-1H-imidazole (Compound 1)

$^1$H NMR (cis isomer as HCl-salt, DMSO-$d_6$): 1.64–1.72 (m,1H), 2.51–2.58 (m, 1H), 2.82 (dd, J=15.0 Hz, J=9.6 Hz, 1H), 3.45 (dd, J=15.0 Hz, J=4.3 Hz, 1H), 3.49–3.57 (m, 1H), 4.24–4.29 (m, 1H), 6.79 (d, J=7.5 Hz, 1H), 7.16–7.35 (m, 8H), 7.47 (d, J=1.3 Hz, 1H), 8.99 (d, J=1.3 Hz, 1H)

4-(5,6-Dimethoxy-3-phenylindan-1-ylmethyl)-1H-imidazole (Compound 2)

$^1$H NMR (cis isomer as HCl-salt, MeOH-$d_4$): 1.61–1.71 (m, 1H), 2.62–2.72 (m, 1H), 2.91 (dd, J=15.1 Hz, J=9.1 Hz, 1H), 3.43 (dd, J=15.1 Hz, J=4.6 Hz, 1H), 3.49–3.55 (m,1H), 3.66 (s, 3H), 3.85 (s, 3H), 4.21–4.25 (m,1H), 6.43 (s, 1H), 6.92 (s,1H), 7.10–7.33 (m, 6H), 8.79 (d, J=1.1 Hz, 1H)

4-[6-Methoxy-3-(4-methoxyphenyl)indan-1-ylmethyl]-1H-imidazole (Compound 5)

$^1$H NMR (cis isomer as HCl-salt, DMSO-$d_6$): 1.57–1.65 (m, 1H), 2.46–2.54 (m, 1H), 2.80 (dd, J=14.8 Hz, J=9.4 Hz, 1H), 3.44 (dd, J=14.8 Hz, J=4.6 Hz, 1H), 3.46–3.54 (m, 1H), 3.73 (s, 3H), 3.75 (s, 3H), 4.10–4.14 (m, 1H), 6.67 (d, J=8.3 Hz, 1H), 6.74 (dd, J=8.3 Hz, J=2.2 Hz, 1H), 6.85–6.90 (m, 3H), 7.06–7.10 (m, 2H), 7.47 (s, 1H), 9.02 (s, 1H)

4-[3-(4-Methoxyphenyl)indan-1-ylmethyl]-1H-imidazole $^1$H NMR (cis isomer as HCl-salt, DMSO-$d_6$): 1.59-1.70 (m, 1H), 2.46–2.55 (m, 1H), 2.83 (dd, J=14.7 Hz, J=9.5 Hz, 1H), 3.45 (dd, J=14.7 Hz, J=4.7 Hz, 1H), 3.49–3.57 (m, 1H), 3.74 (s, 3H), 4.16–4.22 (m, 1H), 6.78 (d, J=7.3 Hz, 1H), 6.86–6.91 (m, 2H), 7.07–7.12 (m, 2H), 7.13–7.34 (m, 3H), 7.46 (d, J=1.4 Hz, 1H), 9.05 (d, J=1.4 Hz, 1H)

4-[3-(4-Fluorophenyl)indan-1-ylmethyl]-1H-imidazole (Compound 7)

$^1$H NMR (cis isomer as HCl-salt, DMSO-$d_6$): 1.62-1.71 (m, 1H), 2.50–2.57 (m, 1H), 2.83 (dd, J=14.8 Hz, J=9.7 Hz, 1H), 3.46 (dd, J=14.8 Hz, J=4.5 Hz, 1H), 3.53–3.60 (m, 1H), 4.26–4.31 (m, 1H), 6.78 (d, J=7.4 Hz, 1H), 7.13–7.35 (m, 7H), 7.47 (d, J=1.3 Hz, 1H), 9.05 (d, J=1.3 Hz, 1H)

4-[3-(3-Fluorophenyl)indan-1-ylmethyl]-1H-imidazole (Compound 9)

$^1$H NMR (cis isomer as HCl-salt, DMSO-$d_6$): 1.67-1.76 (m, 1H), 2.51–2.58 (m, 1H), 2.85 (dd, J=14.9 Hz, J=9.7 Hz, 1H), 3.46 (dd, J=14.9 Hz, J=4.5 Hz, 1H), 3.53–3.59 (m, 1H), 4.29–4.34 (m, 1H), 6.81 (d, J=7.4 Hz, 1H), 6.99–7.41 (m, 7H), 7.47 (d, J=1.2 Hz, 1H), 9.05 (d, J=1.2 Hz, 1H)

4-[3-(2-Fluorophenyl)indan-1-ylmethyl]-1H-imidazole (Compound 10)

$^1$H NMR (cis isomer as HCl-salt, DMSO-$d_6$): 1.71–1.79 (m, 1H), 2.65–2.72 (m, 1H), 2.95 (dd, J=15.1 Hz, J=9.2 Hz, 1H), 3.43 (dd, J=15.1 Hz, J=4.8 Hz, 1H), 3.58–3.65 (m, 1H), 4.58–4.62 (m, 1H), 6.89 (d, J=7.3 Hz, 1H), 7.06–7.34 (m, 8H), 8.79 (d, J=1.3 Hz, 1H)

4-[3-(3,4-Difluorophenyl)indan-1-ylmethyl]-1H-imidazole (Compound 11)

$^1$H NMR (cis isomer as HCl-salt, DMSO-$d_6$): 1.66–1.75 (m, 1H), 2.50–2.57 (m, 1H), 2.84 (dd, J=14.9 Hz, J=9.7 Hz, 1H), 3.46 (dd, J=14.9 Hz, J=4.4 Hz, 1H), 3.52–3.58 (m, 1H), 4.29–4.33 (m, 1H), 6.81 (d, J=7.4 Hz, 1H), 7.05–7.43 (m, 6H), 7.48 (d, J=1.3 Hz, 1H), 9.05 (d, J=1.3 Hz, 1H)

4-[6-Fluoro-3-(4-fluorophenyl)indan-1-ylmethyl]-1H-imidazole (Compound 15)

$^1$H NMR (cis isomer as HCl-salt, DMSO-$d_6$): 1.65–1.76 (m, 1H), 2.52–2.61 (m, 1H), 2.84 (dd, J=14.8 Hz, J=9.5 Hz, 1H), 3.44 (dd, J=14.8 Hz, J=4.6 Hz, 1H), 3.50–3.56 (m, 1H), 4.23–4.30 (m, 1H), 6.76–7.25 (m, 7H), 7.47 (d, J=1.2 Hz, 1H), 9.00 (d, J=1.2 Hz, 1H)

4-[3-(4-Fluorophenyl)-6-methoxyindan-1-ylmethyl]-1H-imidazole $^1$H NMR (cis isomer as HCl-salt, DMSO-d$_6$): 1.62–1.70 (m, 1H), 2.62–2.69 (m, 1H), 2.91 (dd, J=14.9 Hz, J=9.1 Hz, 1H), 3.46 (dd, J=14.9 Hz, J=4.8 Hz, 1H), 3.52–3.57 (m, 1H), 3.79 (s, 3H), 4.20–4.25 (m, 1H), 6.72–7.20 (m, 7H), 7.34 (d, J=1.3 Hz, 1H), 8.83 (d, J=1.3 Hz, 1H)

4-[3-(4-Fluorophenyl)-6-trifluoromethylindan-1-ylmethyl]-1H-imidazole $^1$H NMR (cis-isomer as HCl-salt, MeOH-d$_4$): 1.74–1.83 (m, 1H), 2.70–2.77 (m, 1H), 2.95 (dd, J=14.9 Hz, J=9.5 Hz, 1H), 3.57 (dd, J=14.9 Hz, J=4.7 Hz, 1H), 3.60–3.65 (m, 1H), 4.36–4.40 (m, 1H), 7.02–7.09 (m, 3H), 7.18–7.23 (m, 2H), 7.39 (d, J=1.1 Hz, 1H), 7.50 (d, J=8.0 Hz, 1H), 7.63 (s, 1H), 8.85 (s, 1H)

4-(6-Fluoro-3-phenylindan-1-ylmethyl)-1H-imidazole $^1$H NMR (cis-isomer as HCl-salt, DMSO-d$_6$): 1.69–1.78 (m, 1H), 2.53–2.60 (m, 1H), 2.85 (dd, J=14.9 Hz, J=9.7 Hz, 1H), 3.47 (dd, J=14.9, J=4.3 Hz, 1H), 3.56–3.63 (m, 1H), 4.21–4.26 (m, 1H), 6.76–7.35 (m, 8H), 7.48 (s, 1H), 9.06 (s, 1H)

$^1$H NMR (trans-isomer as HCl-salt, DMSO-d$_6$): 2.14–2.21 (m, 1H), 2.28–2.35 (m, 1H), 2.86 (dd, J=14.8 Hz, J=9.2 Hz, 1H), 3.14 ((dd, J=14.9 Hz, J=5.2 Hz, 1H), 3.68–3.75 (m, 1H), 4.42–4.46 (m, 1H), 6.92–7.32 (m, 8H), 7.45 (s, 1H), 9.06 (s, 1H)

EXAMPLE 2

4-(3-Phenyl-1,3-dihydroisobenzofuran-1-ylmethyl)-1H-imidazole (Compound 12)

This compound was prepared according to the procedure of Example 1 except that 3-phenylphthalide was used in place of 3-phenyl-1-indanone.

$^1$H NMR (cis isomer as HCl-salt, DMSO-d$_6$,): 3.22 (dd, J=15.4 Hz, J=7.4 Hz, 1H), 3.46 (dd, J=15.4 Hz, J=4.1 Hz, 1H), 5.56–5.60 (m, 1H), 6.10 (s, 1H), 6.94 (d, J=7.4 Hz, 1H), 7.20–7.39 (m, 9H), 9.00 (d, J=1.3 Hz, 1H)

EXAMPLE 3

4-(4-Phenyl-1,2,3,4-tetrahydronaphthalen-1-ylmethyl)-1H-imidazole

This compound was prepared according to the procedure of Example 1 except that 4-phenyl-1-tetralone was used in place of 3-phenyl-1-indanone.

$^1$H NMR (cis-isomer as HCl-salt, DMSO-d$_6$): 1.51–1.57 (m, 1H), 1.70–1.78 (m, 1H), 1.91–1.96 (m, 2H), 3.03 (dd, J=14.8 Hz, J=10.2 Hz, 1H), 3.12 (dd, J=14.8 Hz, J=4.4 Hz, 1H), 3.24-3·31 (m, 1H), 4.04–4.08 (m, 1H), 6.70 (d, J=7.1 Hz, 1H), 7.00–7.45 (m, 9H), 9.06 (d, J=1.3 Hz, 1H)

EXAMPLE 4

3-(1H-imidazol-4-ylmethyl)-1-phenylindan-5-ol (Compound 4)

A mixture of 4-(6-methoxy-3-phenylindan-1-ylmethyl)-1H-imidazole (500 mg) and 48% hydrobromic acid (20 ml) was heated at reflux for 1 hr with stirring. The cooled reaction mixture was poured into water and made basic with ammonium hydroxide solution. The resulting precipitate was filtered and washed with water. The product was purified by flash chromatography (elution with a dichloromethane—methanol gradient).

$^1$H NMR (cis isomer, MeOH-d$_4$): 1.62–1.71 (m. 1H), 2.54–2.61 (m, 1H), 2.74 (dd, J=14.6 Hz, J=8.8 Hz, 1H), 3.22 (dd, J=14.6 Hz, J=5.2 Hz, 1H), 3.40–3.49 (m, 1H), 4.09–4.14 (m, 1H), 6.55–6.77 (m, 4H), 7.12–7.28 (m, 5H), 7.57 (d, J=1.1 Hz, 1H)

$^1$H NMR (trans isomer, MeOH-d$_4$): 2.09–2.16 (m. 1H), 2.29–2.35 (m, 1H), 2.74 (dd, J=14.6 Hz, J=8.8 Hz, 1H), 2.94 (dd, J=14.6 Hz, J=5.4 Hz, 1H), 3.50–3.58 (m, 1H), 4.23–4.28 (m, 1H), 6.53–6.73 (m, 4H), 7.07–7.25 (m, 5H), 7.58 (s, 1H)

Using the same method the following compounds were prepared:

4-[3-(1H-Imidazol-4-ylmethyl)indan-1-yl]phenol $^1$H NMR (cis isomer as HCl-salt, DMSO-d$_6$): 1.58–1.66 (m, 1H), 2.45–2.50 (m, 1H), 2.80 (dd, J=14.7 Hz, J=9.5 Hz, 1H), 3.44 (dd, J=14.7 Hz, J=4.6 Hz, 1H), 3.46–3.52 (m, 1H), 4.11–4.16 (m, 1H), 6.70–6.74 (m, 2H), 6.78 (d, J=7.4 Hz, 1H), 6.95–6.99 (m, 2H), 7.14–7.23 (m, 2H), 7.31 (d, J=7.4 Hz, 1H), 7.47 (d, J=1.3 Hz, 1H), 9.03 (d, J=1.3 Hz, 1H), 9.30 (s, 1H)

1-(1H-Imidazol-4-ylmethyl)-3-phenylindan-5,6-diol (Compound 3)

$^1$H NMR (cis isomer as HCl-salt, MeOH-d$_4$): 1.56–1.66 (m. 1H), 2.57–2.66 (m, 1H), 2.87 (dd, J=15.0 Hz, J=8.9 Hz, 1H), 3.31 (dd, J=15.0 Hz, J=4.9 Hz, 1H), 3.39–3.46 (m, 1H), 4.12–4.17 (m, 1H), 6.28 (s, 1H), 6.69 (s, 1H), 7.13–7.30 (m, 6H), 8.79 (s, 1H) 1-(4-Hydroxyphenyl)-3-(1H-imidazol-4-ylmethyl)indan-5-ol (Compound 6)

$^1$H NMR (cis isomer as HCl-salt, DMSO-d$_6$): 1.52–1.60 (m. 1H), 2.41–2.48 (m, 1H), 2.75 (dd, J=14.7 Hz, J=9.4 Hz, 1H), 3.32 (dd, J=14.7 Hz, J=5.1 Hz, 1H), 3.36–3.43 (m, 1H), 3.99–4.03 (m, 1H), 6.57–6.98 (m, 7H), 7.45 (d, 1.3 Hz, 1H), 9.01 (d, 1.3 Hz, 1H), 9.22 (s, 1H), 9.24 (s, 1H)

1-(4-Fluorophenyl)-3-(1H-imidazol-4-ylmethyl)indan-5-ol (Compound 8)

$^1$H NMR (cis isomer as HCl-salt, DMSO-d$_6$): 1.56–1.64 (m, 1H), 2.47–2.54 (m, 1H), 2.77 (dd, J=14.9 Hz, J=9.6 Hz, 1H), 3.34 (dd, J=14.9 Hz, J=5.0 Hz, 1H), 3.40–3.46 (m, 1H), 4.14–4.18 (m, 1H), 6.55–6.69 (m, 3H), 7.10–7.23 (m, 4H), 7.47 (d, 1.3 Hz, 1H), 9.04 (d, J=1.3 Hz, 1H), 9.33 (s, 1H)

EXAMPLE 5

4-(2-Benzylindan-1-ylmethyl)-1H-imidazole a) 2-Benzylideneindan-1-one

To a solution of 1-indanone (5.0 g) and benzaldehyde (4.1 g) in methanol (40 ml), was added 2.2 ml of 48% aqueous sodium hydroxide solution. The reaction mixture was stirred at room temperature for 0.5 hr. The resulting precipitate was filtered and washed with water. The yield was 7.9 g.

$^1$H NMR (DMSO-d$_6$): 4.14 (s, 2H), 7.47–7.81 (m, 10H)

b) 2-Benzylindan-1-one

2-Benzylideneindan-1-one (6.0 g) was hydrogenated in 100 ml of ethanol using 0.1 g of 10% palladium on carbon as catalyst at room temperature. The catalyst was removed by filtration, and the filtrate was evaporated to dryness.

$^1$H NMR (DMSO-d$_6$): 2.67–2.72 (m, 1H), 2.78–2.83 (m, 1H), 3.01–3.08 (m, 1H), 3.10–3.21 (m, 2H), 7.17–7.68 (m, 9H)

c) 4-(2-Benzylindan-1-ylmethyl)-1H-imidazole

This compound was prepared according to the procedure of Example 1 except that 2-benzylindan-1-one was used in place of 3-phenyl-1-indanone.

$^1$H NMR (cis isomer as HCl-salt, DMSO-d$_6$): 2.47–2.53 (m, 1H), 2.63–2.67 (m, 2H), 2.74–2.82 (m, 1H), 2.86–2.93

(m, 2H), 3.02–3.07 (m, 1H), 3.59–3.65 (m, 1H), 6.75 (d, J=7.4 Hz, 1H), 7.02–7.32 (m, 8H), 7.39 (d, J=1.2 Hz, 1H), 9.07 (d, J=1.2 Hz, 1H)

EXAMPLE 6

4-[(2,3-Dihydro-6-methoxy-2-phenyl-1H-inden-1-yl) methyl]-1H-imidazole (compound 13) and 3-(1H-Imidazol-4-ylmethyl)-2-phenylindan-5-ol (compound 14)

(a) 3-(4-Methoxyphenyl)-2-phenylacrylic acid

A mixture of 4-methoxybenzaldehyde (30.0 g, 0.22 mol), phenylacetic acid (31.5 g, 0.23 mol), and triethylamine (31 ml) in acetic anhydride (75 ml) was heated at 90° C. for 5 hours. After cooling, 18 ml of water was dropped carefully during 15 min. Then, potassium carbonate (243 g) in water (1800 ml) was dropped and the solution was heated at 60° C. for 1 hour. After cooling, the solution was extracted with dichloro-methane. When the aqueous phase was acidified (pH 6–7), the product was precipitated. After stirring at 0° C., the product was filtered and dried.

$^1$H NMR (CDCl$_3$): δ 3.75 (3H, s), 6.68 (2H, d, $^3$J=8.8 Hz), 6.99 (2H, d, $^3$J=9.0 Hz), 7.23–7.26 (2H, m), 7.35–7.42 (3H, m), 7.84 (1H, s)

(b) 3-(4-Methoxyphenyl)-2-phenylpropanoic acid

Palladium on activated carbon (10% wt., 2.77 g) was added to a solution of 3-(4-methoxyphenyl)-2-phenylacrylic acid (27.7 g, 0.11 mol) in acetic acid (1000 ml). The mixture was hydrogenated at ambient temperature. The mixture was filtered through Celite, and the solvent was evaporated. The product was recrystallized from a small amount of ethyl acetate. Melting point 220–221° C.

$^1$H NMR (CDCl$_3$): δ 2.84 (1H, dd, $^2$J$_{gem}$=13.8 Hz, $^3$J=9.5 Hz), 3.23 (1H, dd, $^2$J$_{gem}$=13.9 Hz, $^3$J=5.9 Hz), 3.48 (1H, dd, $^3$J=9.4 Hz, $^3$J=6.1 Hz), 3.67 (3H, s), 6.65 (2H, d, $^3$J=8.7 Hz), 6.87 (2H, d, $^3$J=8.6 Hz), 7.04–7.14 (5H, m)

(c) 3-(4-Methoxyphenyl)-2-phenylpropionyl chloride 3-(4-Methoxyphenyl)-2-phenylpropanoic acid (12.5 g, 0.049 mol) was converted to its acid chloride by treatment with thionyl chloride (8.2 ml) in dry dichloromethane (75 ml) at 40° C. Excess thionyl chloride and dichloromethane were evaporated off. The crude product was used in the next step without purification.

$^1$H NMR (CDCl$_3$): δ 3.02 (1H, dd, $^2$J$_{gem}$=14.1 Hz, $^3$J=7.2 Hz), 3.43 (1H, dd, $^2$J$_{gem}$=14.1 Hz, $^3$J=7.9 Hz), 3.76 (3H, s), 4.22 (1H, t, $^3$J=7.5 Hz), 6.77 (2H, d, $^3$J=8.7 Hz), 6.99 (2H, d, $^3$J=8.7 Hz), 7.23–7.26 (2H, m), 7.30–7.38 (3H, m)

(d) 6-Methoxy-2-phenylindan-1-one

Aluminum chloride (345 mg) and one quarter of the crude 3-(4-methoxyphenyl)-2-phenylpropionyl chloride from the previous step were added to dry dichloromethane (45 ml) at 0° C. After 1 hour aluminum chloride (345 mg) and the second quarter of the acid chloride were added. Stirring was continued and the addition was repeated twice again. After the last addition stirring was continued for half an hour at 0° C. and then 2 hours at room temperature. The reaction mixture was poured into ice-cold diluted acidic water. The organic phase was separated and the water phase was extracted twice with dichloromethane. The combined organic phases were washed with water, 2.5% sodium hydroxide solution in water and again with water. The dichloromethane solution was dried and evaporated.

$^1$H NMR (CDCl$_3$): δ 3.19 (1H, dd, $^2$J$_{gem}$=17.1 Hz, $^3$J=3.8 Hz), 3.62 (1H, dd, $^2$J$_{gem}$=17.1 Hz, $^3$J=8.1 Hz), 3.85 (3H, s), 3.92 (1H, dd, $^3$J=8.1 Hz, $^3$J=3.8 Hz), 7.17–7.19 (2H, m), 7.23–7.27 (3H, m), 7.30–7.34 (2H, m), 7.40–7.43 (1H, m)

(e) 1-Benzyl-5-(6-methoxy-2-phenylindan-1-ylidenemethyl)-1H-imidazole

Titanium(IV)chloride (13.2 ml, 22.8 g, 0.12 mol) was added dropwise to a stirred suspension of activated zinc powder (15.9 g, 0.24 mol) in dry tetrahydrofuran (240 ml) at −5° C. -(−10° C.) under a nitrogen atmosphere. After completion of the addition the resulting mixture was refluxed for 2 hours with stirring. A solution of 6-methoxy-2-phenylindan-1-one (7.54 g, 0.032 mol) and 3-benzyl-3H-imidazole-4-carbaldehyde (7.37 g, 0.040 mol) in dry tetrahydrofuran (110 ml) was added dropwise to a refluxing mixture. After the addition the mixture was refluxed for 5 hours. Then the mixture was cooled to 50° C. and 50 ml of methanol and 25 ml of water was added, respectively. The cooled reaction mixture was made alkaline (pH 8–9) with 50% sodium hydroxide solution in water. The slurry was filtered through Celite, and the filtrate was evaporated to dryness under reduced pressure. Ethyl acetate (100 ml) was added to the residue and the mixture was heated. The cooled mixture was filtered and the filtrate was washed with water. The organic phase was dried and evaporated to dryness. The crude product was used in the next step.

(f) 4-[(2,3-Dihydro-6-methoxy-2-phenyl-1H-inden-1-yl) methyl]-1H-imidazole (Compound 13)

A solution of the crude 1-benzyl-5-(6-methoxy-2-phenylindan-1-ylidenemethyl)-1H-imidazole (1.00 g) in acetic acid (100 ml) was shaken with 10% palladium on charcoal (100 mg) for 7 hours at 80° C. under 3 atm of hydrogen on a Parr hydrogenator. The mixture was filtered through Celite, and the filtrate was evaporated to dryness. The residue was dissolved in water, made alkaline (pH 9) and extracted with ethyl acetate. The combined organic phases were washed with water, dried with sodium sulfate and evaporated under reduced pressure to give a crude product which is the mixture of cis and trans diastereomers of 4-[(2,3-dihydro-6-methoxy-2-phenyl-1H-inden-1-yl) methyl]-1H-imidazole. The product was purified by flash chromatography (elution with a dichloromethane—methanol gradient). The base product was converted to its hydrochloride salt by dissolving the base in ethyl acetate and adding hydrogen chloride in ethyl acetate. The product is the mixture of the diastereomers (cis:trans 94:6, mp. 158–159° C.).

The cis diastereomer as its hydrochloride salt: $^1$H NMR (CD$_3$OD): δ 2.52 (1H, distorted ddd, $^2$J$_{gem}$=15.2 Hz, $^3$J=7.4 Hz, $^4$J=0.8 Hz), 2.67 (1H, distorted ddd, $^2$J$_{gem}$=15.4 Hz, $^3$J=8.0 Hz, $^4$J=0.6 Hz), 3.16 (1H, distorted dd, $^2$J$_{gem}$=15.4 Hz, $^3$J=7.6 Hz), 3.27–3.33 (1H, m), 3.71 (3H, s), 3.76 (1H, m), 3.90 (1H, m), 6.39 (1H, d, J$_{meta}$=2.4 Hz), 6.79 (1H, dd, J$_{orto}$=8.2 Hz, J$_{meta}$=2.5 Hz), 6.96 (1H, d, $^4$J=1.2 Hz), 7.18–7.29 (6H, m), 8.68 (1H, d, $^4$J=1.4 Hz)

(g) 3-(1H-Imidazol-4-ylmethyl)-2-phenylindan-5-ol (Compound 14)

A mixture of 4-[(2,3-dihydro-6-methoxy-2-phenyl-1H-inden-1-yl)methyl]-1H-imidazole (370 mg as base) and 48 wt. % hydrobromic acid (15 ml) was heated at 130–140° C. for 2 hours with stirring. The cooled reaction mixture was poured into water and made basic (pH 8). The resulting precipitate was filtered and washed with water. The product was purified by flash chromatography (elution with a dichloromethane—methanol gradient).

The cis diastereomer: $^1$H NMR (CD$_3$OD): δ 2.37 (1H, distorted ddd, $^2$J$_{gem}$=14.7 Hz, $^3$J=6.2 Hz, $^4$J=0.8 Hz), 2.44 (1H, distorted ddd, $^2$J$_{gem}$=14.7 Hz, $^3$J=8.9 Hz), 3.10 (1H, distorted dd, $^2$J$_{gem}$=15.0 Hz, $^3$J=7.3 Hz), 3.16 (1H, distorted dd, $^2J_{gem}$=15.1 Hz, $^3J$=7.4 Hz), 3.68–3.80 (2H, m), 6.23 (1H, d, $J_{meta}$=2.3 Hz), 6.52 (1H, s), 6.60 (1H, dd, $J_{orto}$=8.1 Hz, $J_{meta}$=2.4 Hz), 7.06 (1H, d, $J_{orto}$=8.1 Hz), 7.14–7.19 (3H, m), 7.21–7.25 (2H, m), 7.63 (1H, d, $^4J$=1.0 Hz)

The trans diastereomer: $^1$H NMR (CD$_3$OD): δ 2.84–2.91 (2H, m), 3.04 (1H, distorted dd, $^2J_{gem}$=14.9 Hz, $^3J$=6.4 Hz), 3.16–3.23 (1H, m), 3.26–3.29 (1H, m), 3.58 (1H, m), 6.55 (1H, d, $J_{meta}$=2.2 Hz), 6.63 (1H, dd, $J_{orto}$=8.6 Hz, $J_{meta}$=2.3 Hz), 6.79 (1H, s), 7.01 (1H, d, $J_{orto}$=8.1 Hz), 7.07–7.13 (3H, m), 7.15–7.21 (2H, m), 7.79 (1H, s)

EXAMPLE 7

4-[(2,3-Dihydro-2-phenyl-1H-inden-1-yl)methyl]-1H-imidazole (Compound 16)

(a) 2,3-Diphenylpropanoic Acid

10% Palladium on charcoal (0.8 g) was added to a solution of α-phenylcinnamic acid (10.0 g, 0.0445 mol) in ethanol (200 ml). The mixture was hydrogenated at ambient temperature. The mixture was filtered through Celite, and the solvent was evaporated.

$^1$H NMR (DMSO-d$_6$): δ 2.94 (1H, dd, $^2J_{gem}$=13.8 Hz, $^3J$=6.9 Hz), 3.29 (1H, dd, $^2J_{gem}$=13.8 Hz, $^3J$=8.5 Hz), 3.86 (1H, dd, $^3J$=8.7 Hz, $^3J$=6.9 Hz), 7.12–7.25 (6H, m), 7.28–7.34 (4H, m)

(b) 2-Phenylindan-1-one

Polyphosphoric acid (50 g) was heated in an oil bath at 140–145° C. and 2,3-diphenyl-propanoic acid (2.5 g) was added. Heating was continued for 45 min. Water was added. The mixture was cooled and extracted with ethyl acetate. The organic extracts were washed with 1 M NaOH solution and water. After drying the solvent was evaporated under reduced pressure. The product thus obtained was further purified by trituration in heptane.

$^1$H NMR (DMSO-d$_6$): δ 3.21 (1H, dd, $^2J_{gem}$=17.4 Hz, $^3J$=4.2 Hz), 3.69 (1H, dd, $^2J_{gem}$=17.6 Hz, $^3J$=8.3 Hz), 4.01 (1H, dd, $^3J$=8.3 Hz, $^3J$=4.2 Hz), 7.16–7.19 (2H, m), 7.22–7.27 (1H, m), 7.30–7.35 (2H, m), 7.47–7.51 (1H, m), 7.65–7.77 (3H, m)

(c) 1-Benzyl-5-(2-phenylindan-1-ylidenemethyl)-1H-imidazole

1-Benzyl-5-(2-phenylindan-1-ylidenemethyl)-1H-imidazole was prepared as 1-benzyl-5-(6-methoxy-2-phenylindan-1-ylidenemethyl)-1H-imidazole above except that 2-phen-ylindan-1-one was used as a starting material. In this case after evaporation of the filtrate the residue was dissolved in diluted hydrochloric acid. The product was extracted into dichloromethane. The combined organic phases were washed with water, dried over sodium sulfate and evaporated under reduced pressure. The crude product as its hydrochloride salt was used in the next step without purification.

(d) 4-[(2,3-Dihydro-2-phenyl-1H-inden-1-yl)methyl]-1H-imidazole

The crude 1-benzyl-5-(2-phenylindan-1-ylidenemethyl)-1H-imidazole in acetic acid was shaken with palladium on charcoal as 1-benzyl-5-(6-methoxy-2-phenylindan-1-ylidenemethyl)-1H-imidazole above except in this case for 2 days at 60–70° C. under normal pressure. The hydrochloride salt of the purified product was the mixture of the cis and trans diastereomers (cis:trans 96:4).

The cis diastereomer as its hydrochloride salt: $^1$H NMR (DMSO-d$_6$): δ 2.36 (1H, distorted dd, $^2J_{gem}$=15.0 Hz, $^3J$=5.2 Hz), 2.55 (1H, distorted dd, $^2J_{gem}$=15.1 Hz, $^3J$=8.8 Hz), 3.19 (1H, distorted dd, $^2J_{gem}$=15.6 Hz, $^3J$=7.2 Hz), 3.28–3.36 (2H, m), 3.87 s(2H, m), 6.73 (1H, d, $J_{orto}$=7.4 Hz), 7.06–7.11 (2H,m), 7.18–7.36 (7H, m), 8.95 (1H, d, $^4J$=1.3 Hz)

EXAMPLE 8

4-[(3-Cyclohexyl-2,3-dihydro-1H-inden-1-yl)methyl]-1H-imidazole (a) 3-Cyclohexylindan-1-one This compound was prepared according to the method described by B. M. Trost and L. H. Latimer in *J. Org. Chem.* 42 (1977) 3212. The starting compounds were 1-indanone and cyclohexyl bromide.

$^1$H NMR (CDCl$_3$): δ 0.83–1.35 (6H, m), 1.65–1.90 (5H, m), 2.51 (1H, dd, $^2J_{gem}$=19.1 Hz, $^3J$=3.0 Hz), 2.67 (1H, dd, $^2J_{gem}$=19.1 Hz, $^3J$=7.8 Hz), 3.38 (1H, m), 7.36 (1H, m), 7.49 (1H, m), 7.59 (1H, m), 7.73 (1H, m)

(b) 1-Benzyl-5-(3-cyclohexylindan-1-ylidenemethyl)-1H-imidazole

1-Benzyl-5-(3-cyclohexylindan-1-ylidenemethyl)-1H-imidazole was prepared as 1-benzyl-5-(2-phenylindan-1-ylidenemethyl)-1H-imidazole above except that 3-cyclohexylindan-1-one was used as a starting material. The crude product as its hydro-chloride salt was used in the next step without purification.

(c) 4-[(3-Cyclohexyl-2,3-dihydro-1H-inden-1-yl)methyl]-1H-imidazole

4-[(3-Cyclohexyl-2,3-dihydro-1H-inden-1-yl)methyl]-1-imidazole was prepared as 4-[(2,3-dihydro-6-methoxy-2-phenyl-1H-inden-1-yl)methyl]-1-imidazole above except that 1-benzyl-5-(3-cyclohexylindan-1-ylidenemethyl)-1H-imidazole was used as a starting material. The crude product which is the mixture of cis and trans diastereomers of 4-[(3-cyclohexyl-2,3-dihydro-1H-inden-1-yl)methyl]-1H-imidazole was purified by flash chromatography (eluent: 9.75:0.25 (v/v) mixture of dichloromethane-methanol). The free base was converted to its hydrochloride salt which was the mixture of the diastereomers (cis:trans 98:2).

The cis diastereomer as its hydrochloride salt: $^1$H NMR (CD$_3$OD): δ 0.92 (1H, m), 1.10–1.43 (5H, m), 1.46 (1H, dt, $^3J$=12.4 Hz, $^3J$=9.5 Hz), 1.67–1.84 (4H, m) 1.92 (1H, m), 2.18 (1H, dt, $^3J$=12.4 Hz, $^3J$=7.7 Hz), 2.86 (1H, dd, $^2J_{gem}$=14.6 Hz, $^3J$=8.7 Hz), 3.10 (1H, m), 3.34–3.45 (2H, m), 7.16–7.21 (4H, m), 7.31 (1H, d, $^4J$=1.2 Hz), 8.82 (1H, d, $^4J$=1.4 Hz)

EXAMPLE 9

4-[(3-Benzyl-2,3-dihydro-1H-inden-1-yl)methyl]-1H-imidazole (a) 3-Benzylindan-1-one This compound was prepared according to the method described by B. M. Trost and L. H. Latimer in J. Org. Chem. 42 (1977) 3212. The starting compounds were 1-indanone and benzyl bromide.

$^1$H NMR (CDCl$_3$): δ 2.44 (1H, dd, $^2J_{gem}$=19.2 Hz, $^3J$=3.1 Hz), 2.76 (1H, dd, $^2J_{gem}$=19.2 Hz, $^3J$=7.5 Hz), 2.82 (1H, dd, $^2J_{gem}$=13.8 Hz, $^3J$=9.1 Hz), 3.17 (1H, dd, $^2J_{gem}$=13.8 Hz, $^3J$=6.0 Hz), 3.72 (1H, m), 7.16–7.19 (2H, m), 7.22–7.41 (5H, m), 7.57 (1H, td, $J_{orto}$=7.5 Hz, $J_{meta}$=1.2 Hz), 7.74 (1H, d, $J_{orto}$=7.6 Hz)

(b) 1-Benzyl-5-(3-benzylindan-1-ylidenemethyl)-1H-imidazole

1-Benzyl-5-(3-benzylindan-1-ylidenemethyl)-1H-imidazole was prepared as 1-benzyl-5-(2-phenylindan-1-ylidenemethyl)-1H-imidazole above except that 3-benzylindan-1-one was used as a starting material. The crude product as its hydrochloride salt was used in the next step without purification.

(c) 4-[(3-Benzyl-2,3-dihydro-1H-inden-1-yl)methyl]-1H-imidazole

4-[(3-Benzyl-2,3-dihydro-1H-inden-1-yl)methyl]-1H-imidazole was prepared as 4-[(2,3-dihydro-6-methoxy-2-phenyl-1H-inden-1-yl)methyl]-1H-imidazol above except that 1-benzyl-5-(3-benzylindan-1-ylidenemethyl)-1H-imidazole was used as a starting material. The crude product which is the mixture of cis and trans diastereomers of 4-[(3-benzyl-2,3-dihydro-1H-inden-1-yl)methyl]-1H-imidazole was purified by flash chromatography (eluent: 9.75:0.25 (v/v) mixture of dichloromethane-methanol). The free base was converted to its hydrochloride salt which was the mixture of the diastereomers (cis:trans 86:14).

The cis diastereomer as base: $^1$H NMR (CDCl$_3$): 61.40 (1H, dt, $^2J_{gem}$=12.7 Hz, $^3J$=9.1 Hz), 2.29 (1H, dt, $^2J_{gem}$=12.7 Hz, $^3J$=7.5 Hz), 2.58 (1H, dd, $^2J_{gem}$=13.7 Hz, $^3J$=9.5 Hz), 2.75 (1H, dd, $^2J_{gem}$=14.8 Hz, $^3J$=8.5 Hz), 3.19 (1H, dd, $^2J_{gem}$=15.4 Hz, $^3J$=5.2 Hz), 3.25 (1H, dd, $^2J_{gem}$=13.7 Hz, $^3J$=5.3 Hz), 3.36–3.47 (2H, m), 6.77 (1H, d, $^4J$=0.7 Hz), 7.14–7.31 (9H, m), 7.53(1H, d, $^4J$=0.8 Hz)

EXAMPLE 10

4-(4-Phenyl-1,2,3,4-tetrahydronaphthalen-1-yl)-1H-imidazole (a) 1-(3-Benzyl-3H-imidazol-4-yl)-4,4-diphenylbutan-1-ol Magnesium turnings (0.5 g) were covered with dry tetrahydrofuran (4 ml). 1-Bromo-3,3-diphenylpropane (5.6 g) in 20 ml of dry tetrahydrofuran was added dropwise. The mixture was stirred at reflux for one hour. After being cooled to room temperature, 3-benzyl-3H-imidazole-4-carbaldehyde (3.8 g) in 20 ml of dry tetrahydrofuran was added dropwise to the Grignard reagent and the mixture was refluxed for two hours. The cooled reaction mixture was poured into a cold diluted hydrochloric acid solution. Work-up of the mixture gave the crude product, which was converted to its hydrochloride salt in ethyl acetate using dry hydrochloric acid.

$^1$H NMR (as HCl-salt, DMSO-d$_6$): 1.51–1.59 (m, 2H), 1.86–1.92 (m, 1H), 1.99–2.06 (m, 1H), 3.78 (t, J=7.9 Hz, 1H), 4.51 (m, 1H), 5.36 (s, 2H), 5.51 (s, 1H), 7.14–7.39 (m, 16H), 8.46 (s, 1H)

(b) 1-(1H-Imidazol-4-yl)-4,4-diphenylbutan-1-ol 3.0 g of 1-(3-benzyl-3H-imidazol-4-yl)-4,4-diphenylbutan-1-ol was dissolved in 150 ml of ethanol. The solution was hydrogenated at 45° C. with 10% palladium on carbon as catalyst for 5 hours. The reaction mixture was filtered, and the filtrate was evaporated to dryness under reduced pressure.

$^1$H NMR (as HCl-salt, DMSO-d$_6$): 1.58–1.64 (m, 2H), 1.91–2.01 (m, 1H), 2.08–2.17 (m, 1H), 3.91 (t, J=7.9 Hz, 1H), 4.65 (t, J=6.4 Hz, 1H), 5.49 (s, 1H), 7.12–7.28 (m, 11H), 8.51 (s, 1H)

(c) 4-(4-Phenyl-1,2,3,4-tetrahydronaphthalen-1-yl)-1H-imidazole

A mixture of 1-(1H-imidazol-4-yl)-4,4-diphenylbutan-1-ol hydrochloride (2.0 g) and methanesulfonic acid (40 ml) was heated at 100° C. for 40 minutes. The cooled reaction mixture was poured into water and was made alkaline with sodium hydroxide solution. The product was extracted into ethyl acetate, which was washed with water, dried with sodium sulfate and evaporated under reduced pressure to give a crude product of racemic cis and trans diastereomers. The product was purified by flash chromatography (elution with a dichloromethane—methanol gradient). The base product was dissolved in ethyl acetate and converted to its hydrochloride salt with hydrogen chloride gas.

$^1$H NMR (trans isomer as HCl-salt, MeOH-d$_4$): 1.93–2.04 (m, 2H), 2.21–2.28 (m, 2H), 4.25–4.29 (m, 1H), 4.52–4.56 (m, 1H), 6.90–7.31 (m, 10H), 8.80 (d, J=1,4 Hz, 1H)

$^1$H NMR (cis isomer as HCl-salt, MeOH-d$_4$): 1.74–1.85 (m, 2H), 2.08–2.18 (m, 2H), 4.16–4.20 (m, 1H), 4.42–4.45 (m, 1H), 6.88–7.30 (m, 10H), 8.84 (d, J=1,4 Hz, 1H)

EXAMPLE 11

4-[3-(4-Fluorophenyl)-2,3-dihydro-1H-inden-1-yl]-1H-imidazole (a) trans-3-(4-Fluorophenyl)-1-phenylpropenone A solution of 3.8 g (0.095 mol) of sodium hydroxide in 38 ml of water was dropped gradually into the solution of acetophenone (9.0 g, 0.075 mol) and 4-fluorobenz-aldehyde (9.4 g, 0.076 mol) in ethanol (20 ml). The mixture was stirred for 2 hr at room temperature. Water (80 ml) was added and the mixture was neutralized with 6 M HCl solution. The precipitated trans-3-(4-fluorophenyl)-1-phenylpropenone was filtered, washed with water and dried.

$^1$H NMR (DMSO-d$_6$): δ 7.31 (2H, t, $^3J$=8.9 Hz), 7.59 (2H, t, $^3J$=7.5 Hz), 7.68 (1H, t, $^3J$=7.3 Hz), 7.76 (1H, d, $^3J_{trans}$=15.7 Hz), 7.92 (1H, d, $^3J_{trans}$=15.5 Hz), 7.99 (2H, m), 8.16 (2H, m)

(b) 3-(4-Fluorophenyl)indan-1-one Polyphosphoric acid (102 g) was heated in an oil bath at 140° C. and 3-(4-fluorophenyl)-1-phenylpropenone (5.9 g) was added. Heating was continued for 30 min at 140° C. The mixture was cooled to 80° C. and water was added carefully. The mixture was extracted with ethyl acetate. The organic extracts were washed with water. After drying over sodium sulfate the solvent was evaporated under reduced pressure. The 3-(4-fluorophenyl)indan-1-one obtained was recrystallized from heptane-ethyl acetate 8:2.

$^1$H NMR (CDCl$_3$): δ 2.64 (1H, dd, $^2J_{gem}$=19.2 Hz, $^3J$=3.9 Hz), 3.23 (1H, dd, $^2J_{gem}$=19.2 Hz, $^3J$=8.1 Hz), 4.57 (1H, dd, $^3J$=8.0 Hz, $^3J$=3.9 Hz), 7.00 (2H, distorted t, $^3J$=8.7 Hz), 7.06–7.11 (2H, m), 7.25 (1H, m), 7.43 (1H, t, J$_{orto}$=7.4 Hz), 7.58 (1H, td, J$_{orto}$=7.5 Hz, J$_{meta}$=1.2 Hz), 7.82 (1H, d, J$_{orto}$=7.7 Hz)

(c) 3-(4-Fluorophenyl)-1-(1-trityl-1H-imidazol-4-yl)indan-1-ol

A 3.0 M solution of ethylmagnesium bromide (5.9 ml, 0.0177 mol) in diethyl ether was added to a solution of 4-iodo-1-trityl-1H-imidazole (7.22 g, 0.0165 mol, prepared according to K. L. Kirk J. Heterocycl. Chem. 22 (1985) 57) in 70 ml of dry methylene chloride at ambient temperature. After one hour, a solution of 3-(4-fluorophenyl)indan-1-one (2.00 g, 0.00884 mol) in 6 ml of dry methylene chloride was added and stirring was continued for 45 hr. Saturated ammonium chloride solution was added to quench the reaction. The methylene chloride phase was separated and the aqueous phase was extracted twice with methylene chloride. The combined organic extracts were washed with brine, dried and concentrated. The crude 3-(4-fluorophenyl)-1-(1-trityl-1H-imidazol-4-yl)indan-1-ol was purified by flash chromatography using methylene chloride as an eluent.

(d) 4-[3-(4-Fluorophenyl)-3H-inden-1-yl]-1H-imidazole 3-(4-Fluorophenyl)-1-(1-trityl-1H-imidazol-4-yl)indan-1-ol (2.22 g) in 22 ml of a 2 M HCl solution was heated at 70° C. for 2 hr. Water was added. The mixture was extracted with methylene chloride. Then methylene chloride phase was extracted with 2 M HCl solution. All combined water layers were made basic and extracted with methylene chloride. The organic phase was washed with water and dried. The solvent was removed under reduced pressure. The crude 4-[3-(4-fluorophenyl)-3H-inden-1-yl]-1H-imidazole which was the mixture of isomers (the ratio 73:27) was purified by flash chromatography (elution with a dichloromethane-methanol gradient).

(e) 4-[3-(4-Fluorophenyl)-2,3-dihydro-1H-inden-1-yl]-1H-imidazole

The mixture of the isomers of 4-[3-(4-fluorophenyl)-3H-inden-1-yl]-1H-imidazole was hydrogenated in ethanol using 10% palladium on charcoal as a catalyst. The mixture was filtered through Celite, and the solvent was evaporated. The crude 4-[3-(4-fluorophenyl)-2,3-dihydro-1H-inden-1-yl]-1H-imidazole which was the mixture of the cis and trans diastereomers (the ratio 95.5:4.5) was purified by flash chromatography (elution with a dichloromethane-methanol gradient).

The cis diastereomer as base: $^1$H NMR (CDCl$_3$): δ 2.14 (1H, dt, $^2J_{gem}$=11.1 Hz, $^3J$=11.0 Hz), 2.89 (1H, dt, $^2J_{gem}$=12.3 Hz, $^3J$=7.1 Hz), 4.30 (1H, dd, $^3J$=10.8 Hz, $^3J$=7.2 Hz), 4.44 (1H, dd, $^3J$=10.8 Hz, $^3J$=7.2 Hz), 6.87–6.90 (2H, m), 6.96 (2H, t, $^3J$=8.7 Hz), 7.12–7.19 (5H, m), 7.43 (1H, s)

EXAMPLE 12

4-(3-Benzyl-2,3-dihydro-1H-inden-1-yl)-1H-imidazole

3-Benzyl-1-(1-trityl-1H-imidazol-4-yl)indan-1-ol

This compound was obtained from 4-iodo-1-trityl-1H-imidazole and 3-benzylindan-1-one by the method described for 3-(4-fluorophenyl)-1-(1-trityl-1H-imidazol-4-yl)indan-1-ol as stated above. The 3-benzyl-1-(1-trityl-I H-imidazol-4-yl)indan-1-ol was purified by flash chromatography (the eluent: heptane-ethyl acetate 1:1).

4-(3-Benzyl-3H-inden-1-yl)-1H-imidazole

Triethylsilane (1 ml, 0.728 g, 6.26 mmol) and trifluoroacetic acid (1.9 ml, 2.81 g, 24.7 mmol) were added to the solution of 3-benzyl-1-(1-trityl-1H-imidazol-4-yl)indan-1-ol (0.387 g, 0.73 mmol) in dichloromethane (13 ml). The reaction was stirred at room temperature for 20 hr. Then the reaction was quenched with water and made basic with the 2 M sodium hydroxide solution. The dichloromethane layer was washed with water and dried over sodium sulfate. The solvent was removed under reduced pressure. Flash chromatography using a dichloromethane-methanol gradient afforded 4-(3-benzyl-3H-inden-1-yl)-1H-imidazole.

$^1$H NMR (CDCl$_3$): δ 2.69 (1H, dd, $^2J_{gem}$=13.5 Hz, $^3J$=9.4 Hz), 3.13 (1H, dd, $^2J_{gem}$=13.5 Hz, $^3J$=6.7 Hz), 3.80 (1H, m), 6.64 (1H, d, $^3J$=2.2 Hz), 7.16–7.33 (7H, m), 7.37 (1H, s), 7.60 (1H, d, $^3J$=0.6 Hz), 7.69 (1H, d, J$_{orto}$=7.6 Hz)

4-(3-Benzyl-2,3-dihydro-1H-inden-1-yl)-1H-imidazole 4-(3-benzyl-3H-inden-1-yl)-1H-imidazole was hydrogenated in ethanol using 10% palladium on charcoal as a catalyst. The mixture was filtered through Celite, and the solvent was evaporated. The crude 4-(3-benzyl-2,3-dihydro-1H-inden-1-yl)-1H-imidazole which was the mixture of the cis and trans diastereomers (the ratio 94:6) was purified by flash chromatography (elution with a dichloromethane—methanol gradient).

The cis diastereomer as base: $^1$H NMR (CDCl$_3$): δ 1.82 (1H, dt, $^2J_{gem}$=12.5 Hz, $^3J$=9.7 Hz), 2.53 (1H, dt, $^2J_{gem}$=12.5 Hz, $^3J$=7.4 Hz), 2.69 (1H, dd, $^2J_{gem}$=13.6 Hz, $^3J$=9.4 Hz,), 3.31 (1H, dd, $^2J_{gem}$=13.6 Hz, $^3J$=5.3 Hz), 3.49 (1H, m), 4.31 (1H, m), 6.80 (1H, s), 7.08 (1H, distorted d, J$_{orto}$=7.4 Hz), 7.15–7.30 (8H, m), 7.46 (1H, m)

EXAMPLE 13

4-(2,3-Dihydro-3-phenylinden-1-yl)-1H-imidazole 2-(tert-Butyidimethylsilanyl)-5-(2,3-dihydro-1-hydroxy-3-phenyl-1H-inden-1-yl)-1H-imidazole-1-sulfonic acid dimethylamide A solution of imidazole-1-sulfonic acid dimethylamide (1.96 g, 0.0112 mol, prepared according to D. J. Chadwick and R. I. Ngochindo *J. Chem. Soc. Perkin Trans. I* (1984) 481) in dry tetrahydrofuran (90 ml) under nitrogen was cooled to −78° C. and treated dropwise with 15% n-butyllithium in hexane (8.2 ml, 0.01393 mol). After 30 minutes tert-butyldimethylsilyl chloride (2.1 g, 0.01393 mol) in dry tetrahydrofuran (5 ml) was added and the mixture was allowed to warm to room temperature. After 1.5 hr the mixture was again cooled to −78° C. and treated with 15 % n-butyllithium in hexane (8.5 ml, 0.01360 mol). After 30 minutes 3-phenyl-1-indanone (3.40 g, 0.01633 mol) in dry tetrahydrofuran was added and the mixture was allowed to warm to room temperature during the night. The mixture was quenched with saturated sodium carbonate solution and the solvent was removed under reduced pressure. The residue was dissolved in dichloromethane and washed twice with water, dried, filtered and concentrated under reduced pressure. Purification was done by flash chromatography (elution with a heptane—ethyl acetate gradient).

$^1$H NMR (CDCl$_3$): δ 0.40 (3H, s), 0.41 (3H, s), 0.98 (9H, s), 2.47 (1H, dd, $^2J_{gem}$=12.9 Hz, $^3J$=10.0 Hz), 2.88 (6H, s), 3.24 (1H, dd, $^2J_{gem}$=12.9 Hz, $^3J$=7.2 Hz), 4.05 (1H, dd $^3J$=9.9 Hz $^3J$=7.3 Hz), 6.14 (1H, s), 6.92 (1H, d, J$_{orto}$=7.0 Hz), 7.20–7.36 (7H, m), 7.52 (1H, d, J$_{orto}$=7.0 Hz)

5-(2,3-Dihydro-1-hydroxy-3-phenyl-1H-inden-1-yl)-1H-imidazole-1-sulfonic acid dimethylamide A 1.1 M solution of tetrabutylammonium fluoride in tetrahydrofuran (1.4 ml, 1.54 mmol) was added dropwise to the solution of 2-(tert-butyldimethylsilanyl)-5-(2,3-dihydro-1-hydroxy-3-phenyl-1H-inden-1-yl)-1H-imidazole-1-sulfonic acid dimethylamide (637 mg, 1.28 mmol) in tetrahydrofuran (13 ml). The reaction was stirred overnight at room temperature. The reaction was quenched with water and then extracted with ethyl acetate. The organic layer was washed with water and brine. The organic phase was dried and the solvent removed under reduced pressure. The product was recrystallized in ethyl acetate.

$^1$H NMR (CDCl$_3$): δ 2.47 (1H, dd, $^2J_{gem}$=13.0 Hz, $^3J$=10.0 Hz), 3.04 (6H, s), 3.31 (1H, dd, $^2J_{gem}$=12.9 Hz, $^3J$=7.2 Hz), 4.09 (1H, dd, $^3J$=9.9 Hz, $^3J$=7.2 Hz), 6.07 (1H, s), 6.96 (1H, d, J$_{orto}$=7.6 Hz), 7.19–7.27 (4H, m), 7.30–7.40 (3H, m), 7.54 (1H, d, J$_{orto}$=6.8 Hz), 7.94 (1H,s)

5-(3-Phenyl-3H-inden-1-yl)-1H-imidazole-1-sulfonic acid dimethylamide

Triethylsilane (760 μl, 554 mg, 4.77 mmol) and trifluoroacetic acid (1.43 ml, 2.12 g, 18.6 mmol) were added to the solution of 5-(2,3-dihydro-1-hydroxy-3-phenyl-1H-inden-1-yl)-1H-imidazole-1-sulfonic acid dimethylamide (230 mg, 0.60 mmol) in dichloromethane (8 ml). The reaction was stirred overnight at room temperature. Then the reaction was quenched with water and made basic with the 2 M sodium hydroxide solution. The dichloromethane layer was washed with water and dried over sodium sulfate. The solvent was removed under reduced pressure. Purification by flash chromatography using a dichloromethane-methanol gradient afforded the mixture of the isomers (the ratio 65:35) of 5-(3-phenyl-3H-inden-1-yl)-1H-imidazole-1-sulfonic acid dimethylamide.

23

4-(3-Phenyl-3H-inden-1-yl)-1H-imidazole 5-(3-Phenyl-3H-inden-1-yl)-1H-imidazole-1-sulfonic acid dimethylamide (158 mg, 0.43 mmol) in 5 ml of a 1.5 M HCl solution was refluxed for 1.5 hr. The reaction mixture was made basic and then extracted with ethyl acetate. The organic phase was washed with water and dried. The solvent was removed under reduced pressure. The crude 4-(3-phenyl-3H-inden-1-yl)-1H-imidazole which was the mixture of isomers (the ratio 75:25) was purified by flash chromatography (elution with dichloromethane-methanol 9.75:0.25).

4-(2,3-Dihydro-3-phenylinden-1-yl)-1H-imidazole

The mixture of the isomers of 4-(3-phenyl-3H-inden-1-yl)-1H-imidazole was hydrogenated in acetic acid at 50° C. using 10% palladium on charcoal as a catalyst. The mixture was filtered through Celite, and the solvent was evaporated. Water was added and the solution was made basic. The water solution was extracted with ethyl acetate. The organic phase was washed with water, dried and the solvent was evaporated. The hydrochloride salt of the product was made in ethyl acetate. The product 4-(2,3-dihydro-3-phenylinden-1-yl)-1H-imidazole was the mixture of the cis and trans diastereomers (the ratio 95:5).

The cis diastereomer as its hydrochloride salt: $^1$H NMR (CD$_3$OD): δ 2.19 (1H, dt, $^2J_{gem}$=12.2 Hz, $^3J$=11.0 Hz), 2.99 (1H, dt, $^2J_{gem}$=12.2 Hz, $^3J$=7.1 Hz), 4.43 (1H, dd, $^3J$=10.9 Hz, $^3J$=7.0 Hz), 4.66 (1H, dd, $^3J$=11.0 Hz, $^3J$=7.0 Hz), 6.92–6.94 (1H, m), 7.07–7.09 (1H, m), 7.23–7.37 (7H, m), 7.52 (1H, d, $^4J$=1.2 Hz), 8.89 (1H, d, $^4J$=1.4 Hz)

EXAMPLE 14

4-[(1,2,3,4-Tetrahydro-3-phenyinaphthalen-1-yl)methyl]-1H-imidazole

1-Benzyl-5-(3-phenyl-3,4-dihydro-2H-naphthalen-1-ylidenemethyl)-1H-imidazole

1-Benzyl-5-(3-phenyl-3,4-dihydro-2H-naphthalen-1-ylidenemethyl)-1H-imidazole was prepared as 1-benzyl-5-(2-phenylindan-1-ylidenemethyl)-1H-imidazole above except that 3-phenyl-3,4-dihydro-2H-naphthalen-1-one (prepared according to J. Vebrel and R. Carrie *Bull. Soc. Chem. Fr.* (1982) 116) was used as a starting material. The crude product as its hydrochloride salt was used in the next step without purification.

4-[(1,2,3,4-Tetrahydro-3-phenyinaphthalen-1-yl)methyl]-1H-imidazole 4-[(1,2,3,4-Tetrahydro-3-phenyinaphthalen-1-yl)methyl]-1H-imidazole was prepared as 4-[(2,3-dihydro-6-methoxy-2-phenyl-1H-inden-1-yl)methyl]-1H-imidazole above except that 1-benzyl-5-(3-phenyl-3,4-dihydro-2H-naphthalen-1-ylidenemethyl)-1H-imidazole was used as a starting material. The hydrochloride salt of the product was the mixture of two diastereomers (82:18, mp. 198° C.).

24

We claim:
1. An imidazole derivative of formula (I):

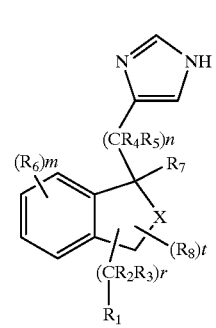

(I)

wherein X is —CH$_2$—(CH$_2$)$_p$—, —O—, =NH or —S—;

R$_1$ is phenyl, naphthyl, 1,2,3,4-tetrahydronaphthyl, C$_3$-C$_7$-cycloalkyl, C$_5$-C$_7$-cycloalkenyl, C$_5$-C$_7$-cycloalkynyl or a mono- or bicyclic aromatic or partially or fully saturated heterocyclic group with 5 to 10 ring atoms which are carbon atoms and one to three heteroatoms selected from N, O and S;

wherein the said phenyl, naphthyl,1,2,3,4-tetrahydronaphthyl, C$_3$-C$_7$-cycloalkyl, C$_5$-C$_7$-cycloalkenyl, C$_5$-C$_7$-cycloalkynyl or mono- or bicyclic aromatic or partially or fully saturated heterocyclic group is optionally substituted with one to three substituents selected independently from halogen, —OH, —NH$_2$, halo-C$_1$-C$_6$-alkyl, C$_1$-C$_6$-alkyl, C$_2$-C$_6$-alkenyl, C$_2$-C$_6$-alkynyl, C$_1$-C$_6$-alkoxy, OH—(C$_1$-C$_6$)-alkyl, NH$_2$—(C$_1$-C$_6$)-alkyl and mono- or di(C$_1$-C$_6$-alkyl) amino;

R$_2$ is H or C$_1$-C$_6$-alkyl;

R$_3$ is H or C$_1$-C$_6$-alkyl;

R$_4$ is H or C$_1$-C$_6$-alkyl;

R$_5$ is H, or R$_5$ and R$_7$ form together a bond;

each R$_6$ is independently halogen, —OH, —NH$_2$, halo-C$_1$-C$_6$-alkyl, C$_1$-C$_6$-alkyl, C$_1$-C$_6$-alkoxy or OH—(C$_1$-C$_6$)-alkyl;

R$_7$ is H, OH or C$_1$-C$_4$-alkyl, or R$_7$ and R$_5$ form together a bond;

each R$_8$ is independently OH, C$_1$-C$_6$-alkyl, halo-C$_1$-C$_6$-alkyl or C$_1$-C$_6$-alkoxy;

m is 0,1,2 or 3;

n is 0 or 1;

p is 0 or 1;

r is 0 or 1; and t is 0,1 or 2;

or a pharmaceutically acceptable ester or salt thereof.

2. A compound according to claim 1, wherein X is —CH$_2$—(CH$_2$)$_p$— and p is 0.

3. A compound according to claim 1, wherein X is —CH$_2$—(CH$_2$)$_p$— and p is 1.

4. A compound according to claim 1, wherein X is —O—.

5. A compound according to claim 1, which is a compound of formula IA

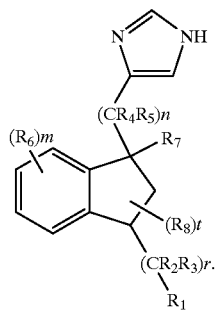

(IA)

6. A compound according to claim 1, which is a compound of formula IB

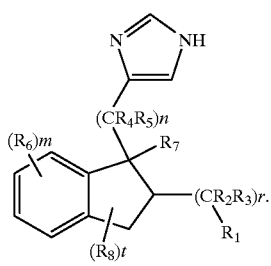

(IB)

7. A compound according to claim 1, wherein r is 0.
8. A compound according to claim 1, wherein r is 1 and $R_2$ and $R_3$ are H.
9. A compound according to claim 1, wherein n is 0.
10. A compound according to claim 1, wherein n is 1.
11. A compound according to claim 1, wherein n is 1 and $R_4$ and $R_5$ are H.
12. A compound according to claim 1, wherein $R_7$ is H.
13. A compound according to claim 1, wherein $R_1$ is phenyl, naphthyl, pyridyl, thienyl, furyl or cyclohexyl; each of which is unsubstiuted or substituted with one to three of the substituents selected independently from halogen, —OH, —$NH_2$, halo-$C_1$-$C_6$-alkyl, $C_1$-$C_6$-alkyl, $C_2$-$C_6$-alkenyl, $C_2$-$C_6$-alkynyl, $C_1$-$C_6$-alkoxy, OH—($C_1$-$C_6$)alkyl, $NH_2$—($C_1$-$C_6$)-alkyl and mono- or di($C_1$-$C_6$-alkyl)amino.
14. A compound according to claim 1, wherein $R_1$ is phenyl, naphthyl, pyridyl, thienyl, furyl or cyclohexyl; each of which is unsubstituted or substituted with one to three of the substituents selected independently from halogen, —OH, $C_1$-$C_6$-alkoxy and $C_1$-$C_6$-alkyl.
15. A compound according to claim 1, wherein $R_1$ is phenyl, pyridyl or cyclohexyl; each of which is unsubstituted or substituted with one to three of the substituents selected independently from halogen, —OH, $C_1$-$C_6$-alkoxy and $C_1$-$C_6$ alkyl.
16. A compound according to claim 1, wherein $R_1$ is phenyl or cyclohexyl; each of which is unsubstituted or substituted with one to three of the substituents selected independently from halogen, —OH, —$NH_2$, halo-$C_1$-$C_6$-alkyl, $C_1$-$C_6$-alkyl, $C_2$-$C_6$-alkenyl, $C_2$-$C_6$-alkynyl, $C_1$-$C_6$-alkoxy, OH—($C_1$-$C_6$)-alkyl, $NH_2$—($C_1$-$C_6$)-alkyl and mono- or di($C_1$-$C_6$-alkyl)amino.
17. A compound according to claim 1, wherein m is 0.
18. A compound according to claim 1, wherein m is 1 or 2 and each $R_6$ is selected independently from halogen, —OH, $C_1$-$C_6$-alkoxy and $C_1$-$C_6$-alkyl.
19. A compound according to claim 1, wherein t is 0.
20. A pharmaceutical composition comprising at least one compound according to claim 1 and at least one pharmaceutically acceptable carrier, diluent excipient, or combination thereof.

21. A method for the treatment of a neurological, psychiatric, or cognition disorder, which comprises administering to a host in need of the treatment an effective amount of at least one compound according to claim 1.
22. A method for the treatment of diabetes, a lipolytic disorder, orthostatic hypotension or sexual dysfunction, which comprises administering to a host in need of the treatment an effective amount of at least one compound according to claim 1.
23. A process for the preparation of a compound of formula I' or Ia according to claim 1, wherein n is 1, which comprises reacting a compound of formula II

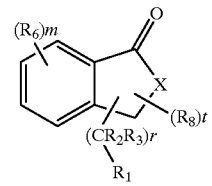

II wherein X, $R_1$ to $R_3$, $R_6$, $R_8$, m, r and t are as defined in claim 1, with a compound of formula III

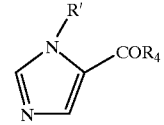

III wherein $R_4$ is as defined in claim 1 and R' is H or a protecting group, to obtain a compound of formula I',

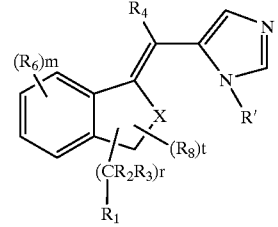

I' wherein X, $R_1$ to $R_4$, $R_6$, $R_8$, m, r, t and R' are as defined above, and either deprotecting the compound of formula I' and isolating the compound, or hydrogenating the compound of formula I' to obtain the compound of formula Ia

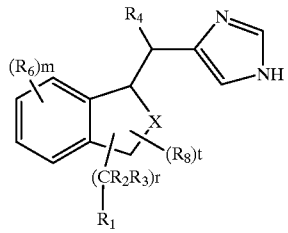

Ia wherein X, $R_1$ to $R_4$, $R_6$, $R_8$, m, r, t and R' are as defined above.

* * * * *